(12) United States Patent
Horn et al.

(10) Patent No.: US 8,144,152 B2
(45) Date of Patent: Mar. 27, 2012

(54) SYSTEM AND METHOD FOR PRESENTATION OF DATA STREAMS

(75) Inventors: Eli Horn, Kiryat Motzkin (IL); Hagal Krupnik, Nofit (IL)

(73) Assignee: Given Imaging, Ltd., Yoqneam (IL)

( * ) Notice: Subject to any disclaimer, the term of this patent is extended or adjusted under 35 U.S.C. 154(b) by 0 days.

(21) Appl. No.: 12/615,794

(22) Filed: Nov. 10, 2009

(65) Prior Publication Data

US 2010/0053313 A1    Mar. 4, 2010

Related U.S. Application Data

(60) Continuation of application No. 11/723,253, filed on Mar. 19, 2007, now Pat. No. 7,636,092, which is a division of application No. 10/950,480, filed on Sep. 28, 2004, now Pat. No. 7,215,338.

(60) Provisional application No. 60/507,508, filed on Oct. 2, 2003.

(51) Int. Cl.
*G06T 11/00* (2006.01)

(52) U.S. Cl. .................... 345/440; 345/440.2

(58) Field of Classification Search .............. 345/440, 345/440.1, 440.2; 348/65, 71, 74; 382/168; 702/180; 358/522; 715/720
See application file for complete search history.

(56) References Cited

U.S. PATENT DOCUMENTS

| | | | |
|---|---|---|---|
| 3,909,792 A * | 9/1975 | Harris et al. ................ | 345/440 |
| 5,333,244 A * | 7/1994 | Harashima ................ | 345/440 |
| 5,519,828 A | 5/1996 | Rayner | |
| 7,219,034 B2 * | 5/2007 | McGee et al. ............... | 702/180 |
| 7,245,746 B2 * | 7/2007 | Bjaerum et al. ............. | 382/168 |
| 7,694,320 B1 * | 4/2010 | Yeo et al. ...................... | 715/720 |
| 2002/0171669 A1 * | 11/2002 | Meron et al. ................. | 345/619 |
| 2003/0063130 A1 * | 4/2003 | Barbieri et al. .............. | 345/833 |
| 2003/0077223 A1 * | 4/2003 | Glukhovsky et al. ......... | 424/9.1 |
| 2004/0066398 A1 * | 4/2004 | Dolimier et al. ............. | 345/720 |
| 2004/0184639 A1 * | 9/2004 | Jackson et al. ............... | 382/111 |
| 2004/0225223 A1 * | 11/2004 | Honda et al. ................ | 600/476 |
| 2004/0249291 A1 * | 12/2004 | Honda et al. ................ | 600/476 |
| 2004/0257620 A1 * | 12/2004 | Loce et al. .................... | 358/2.1 |

FOREIGN PATENT DOCUMENTS

EP    1 618 832    1/2006

OTHER PUBLICATIONS

A. Yoshitaka, T. Ishii, M. Hirakawa, T. Ichikawa, Content-based retrieval of video data by the grammar of film, Sep. 1997, 1997 IEEE Symposium on Visual Languages Proceedings, pp. 310-317.*
Internet Archive Webshots of Feb. 29, 2000 weather.com, printed on Oct. 21, 2010, http://web.archive.org/web/*/http://www.weather.com/, pp. 1-15.*
European Search Report of European Application No. 10181052.1 dated Dec. 14, 2010.

* cited by examiner

*Primary Examiner* — Jeffery A Brier
(74) *Attorney, Agent, or Firm* — Pearl Cohen Zedek Latzer, LLP

(57) ABSTRACT

An in-vivo sensing system and a method for creating a summarized graphical presentation of a data stream captured in-vivo. The graphical presentation may be in the form of for example a color bar. The color bar may be a fixed display along side a streaming display of the data stream. A cursor or other indicator may move along the fixed color bar as the data stream is displayed and/or streamed so as to indicate to a health professional what part of the data stream may be currently displayed. The color content in the color bar may map out the data stream and give indication of the location of anatomical sites as well as possible locations of pathology.

14 Claims, 6 Drawing Sheets

SYSTEM AND METHOD FOR PRESENTATION OF DATA STREAMS

CROSS-REFERENCE TO RELATED APPLICATIONS

This application is a continuation of prior U.S. patent application Ser. No. 11/723,253, filed on Mar. 19, 2007 now U.S. Pat. No. 7,636,092, which in turn is a divisional application of prior U.S. application Ser. No. 10/950,480, filed on Sep. 28, 2004 (now U.S. Pat. No. 7,215,338), which in turn claims benefit from prior U.S. provisional application Ser. No. 60/507,508 filed on Oct. 2, 2003 entitled, "DEVICE, SYSTEM AND METHOD FOR PRESENTATION OF IN-VIVO DATA" all of which are incorporated in its entirety by reference herein.

FIELD OF THE INVENTION

The present invention relates to presentations of data streams and to a system and method for presenting in-vivo data.

BACKGROUND OF THE INVENTION

Known in-vivo imaging devices include ingestible capsules that may capture images from the inside of the gastrointestinal (GI) tract. Captured images may be transmitted to an external source to be examined, for example, for pathology by a healthcare professional. In some embodiments, in-vivo devices may include various other sensors that may transmit data to an external source for monitoring and diagnosis.

An in-vivo device may collect data from different points along a body lumen, for example lumens of the GI tract, and transmit them externally for analysis and diagnosis. The GI tract is a very long and curvy path such that it may be difficult to get a good indication of where along this tract each transmitted datum was obtained.

Time bars are known to be used when reviewing data, so as to indicate to the health professional how far along the image stream he/she may have advanced. However, since the in-vivo device may stall or advance at different speeds through various sections of a body lumen, for example, the GI tract, it may not be positively determined in some cases where or at what distance along the GI tract was a particular datum, for example an image, captured. In addition, on the time bar there may be no indication as to when the device may have reached certain anatomical milestones, for example, the duodenum, the cecum, or other anatomical locations in the GI tract.

Localization methods have been applied. Some localization methods may indicate the spatial position of the device in space at any given time. Although this information together with the time log may give the health professional a better indication of the rate at which the device has advanced it may still be difficult to correlate the spatial position of the device in space to the specific anatomy of, for example, the GI tract.

An in-vivo device may collect data from more than one sensor along the very long and curvy path resulting in multiple data streams captured by the in-vivo sensor. It may be time consuming and difficult to review multiple long streams of data. In addition, it may be difficult for a health profession to get an overall view of the contents of all the data obtained.

SUMMARY OF THE INVENTION

Embodiments of the present invention may provide a system and method for generating and displaying a fixed graphical presentation of captured in-vivo data streams. In one embodiment of the present invention, the fixed graphical presentation is a varying visual representation of a quantity or a dimension captured in an in-vivo data stream. In one example the graphical presentation is in the form of a color bar. In other embodiments of the present invention, the fixed graphical presentation may be displayed along side a streaming display of a data stream.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
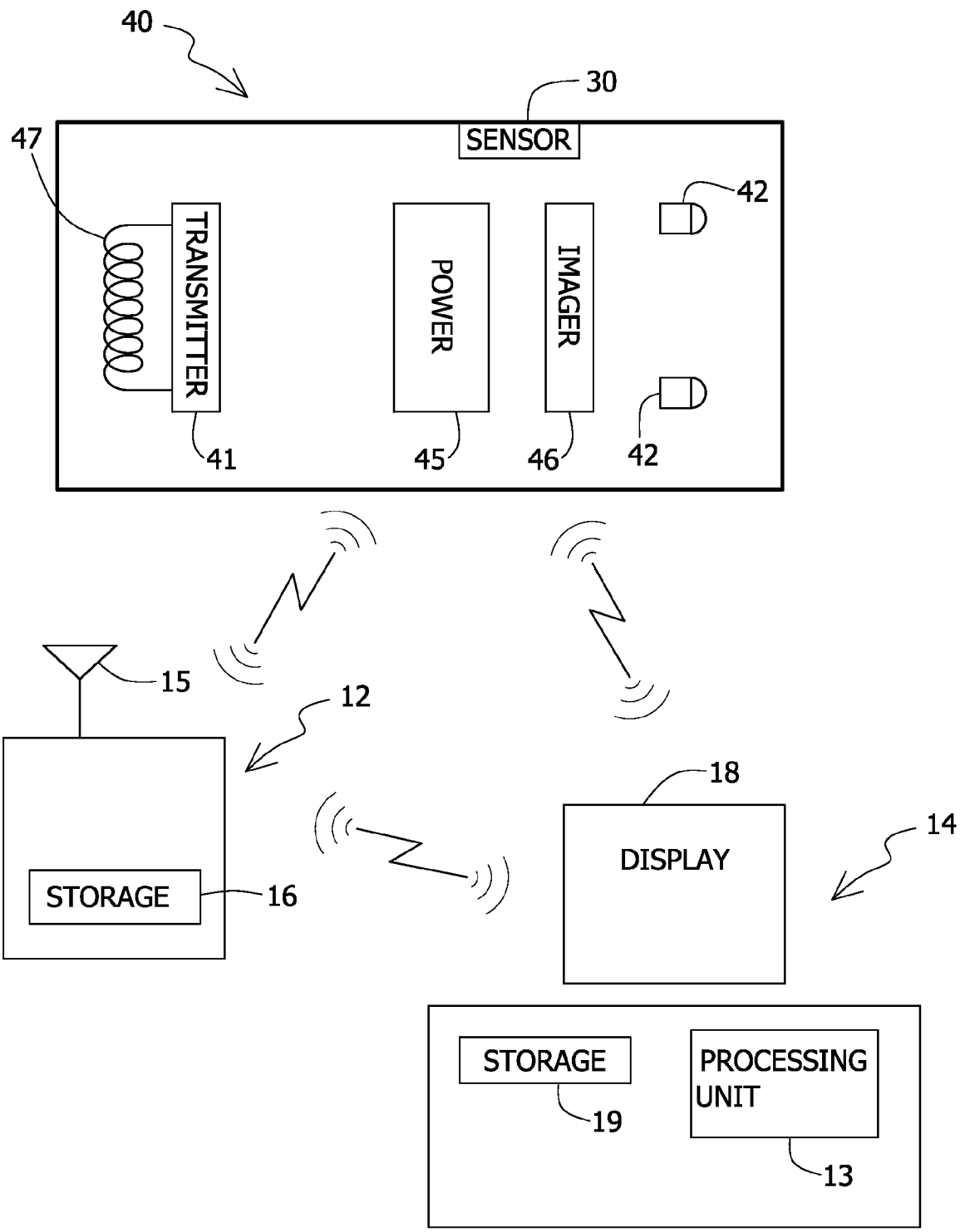
FIG. 1 is a schematic illustration of an in-vivo imaging system in accordance with embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Embodiments of the present invention offer a device, system and method for generating a fixed graphical presentation of a captured data stream, for example image streams, other non-imaged data, or other data such as color coded, possibly imaged data (e.g., pH data, temperature data, etc.) that may have been collected in vivo, for example along the GI tract. The summarized graphical presentation may include, for example, a varying visual representation, for example, a series of colors that may be at least partially representative of a quantity and/or data collected, e.g. a series of colors where each color presented on the bar may representative of a value of a parameter. Other suitable representations may be used, and other visual dimensions or qualities, such as brightness, size, width, pattern, etc. may be used. In some embodiments of the present invention, the summarized graphical presentation may be a fixed display along side a streaming display of the data stream In one embodiment of the invention, the presentation may map out a varying quantity (e.g. a captured data stream) and may, for example, give indication of the relationship between the data stream captured and the anatomical origin or position relative to a start of the captured data stream, for example, the approximate or exact site, for example, in the GI tract from where various data captured may have originated. In another embodiment of the invention, the mapping may give, for example, an indication of an event (e.g. a physiological event) captured, measured, or otherwise obtained. In yet another embodiment of the invention, the mapping may give for example an indication of change of one or more parameters measured over time, for example, a change occurring due to pathology, a natural change in the local environment, or due to other relevant changes. The location may be relative to other information, for example, anatomical attributes along for example the GI tract. The location may in some embodiments be an absolute location, such as a location based on time or based on position of an in-vivo information capture device, based on an image frame in a sequence of images, etc.

Reference is made to FIG. 1, which shows a schematic diagram of an in-vivo sensing system according to one embodiment of the present invention. Typically the in-vivo sensing system, for example, an image sensing system, may include an in-vivo sensing device 40, for example an imaging device having an imager 46, for capturing images, an illumination source 42, for illuminating the body lumen, a power source 45 for powering device 40, and a transmitter 41 with antenna 47, for transmitting image and possibly other data to an external receiving device 12. In some embodiments of the present invention, in-vivo device 40 may include one or more sensors 30 other than and/or in addition to image sensor 46, for example, temperature sensors, pH sensors, pressure sensors, blood sensors, etc. In some embodiments of the present invention, device 40 may be an autonomous device, a capsule, or a swallowable capsule. In other embodiments of the present invention, device 40 may not be autonomous, for example, device 40 may be an endoscope or other in-vivo imaging sensing device.

The in-vivo imaging device 40 may typically, according to embodiments of the present invention, transmit information (e.g., images or other data) to an external data receiver and/or recorder 12 possibly close to or worn on a subject. Typically, the data receiver 12 may include an antenna or antenna array 15 and a data receiver storage unit 16. The data receiver and/or recorder 12 may of course take other suitable configurations and may not include an antenna or antenna array. In some embodiments of the present invention, the receiver may, for example, include processing power and/or a LCD display from displaying image data.

The data receiver and/or recorder 12 may, for example, transfer the received data to a larger computing device 14, such as a workstation or personal computer, where the data may be further analyzed, stored, and/or displayed to a user. Typically, computing device 14 may include processing unit 13, data processor storage unit 19 and monitor 18. Computing device 14 may typically be a personal computer or workstation, which includes standard components such as processing unit 13, a memory, for example storage or memory 19, a disk drive, a monitor 18, and input-output devices, although alternate configurations are possible. Processing unit 13 typically, as part of its functionality, acts as a controller controlling the display of data for example, image data or other data. Monitor 18 is typically a conventional video display, but may, in addition, be any other device capable of providing image or other data. Instructions or software for carrying out a method according to an embodiment of the invention may be included as part of computing device 14, for example stored in memory 19.

In other embodiments, each of the various components need not be required; for example, the in-vivo device 40 may transmit or otherwise transfer (e.g., by wire) data directly to a viewing or computing device 14

In-vivo imaging systems suitable for use with embodiments of the present invention may be similar to various embodiments described in U.S. Pat. No. 5,604,531, assigned to the common assignee of the present application and incorporated herein by reference, and/or Publication Number WO 01/65995, also assigned to the common assignee of the present application and incorporated herein by reference. Other in-vivo systems, having other configurations, may be used. Of course, devices, systems, structures, functionalities and methods as described herein may have other configurations, sets of components, processes, etc.

Embodiments of the present invention include a device, system, and method for generating a typically concise and/or summarized graphical presentation of parameters sensed through or over time in a body lumen, for example the GI tract or any other tract, through which a sensing device may be present and/or traveling. Viewing a data stream captured by an in-vivo device, e.g., viewing an image stream transmitted by an ingestible imaging capsule may be a prolonged procedure. A summarized presentation of the data captured that may, for example, provide a visual representation and/or map of the captured data and may help focus a health professional's attention to an area of interest and/or may promote a health professional's understanding of the origin and contents of the data being viewed.

One or more streams of data obtained from said sensing device may be processed to create one or more summarized presentations that may, for example, be displayed in a graphical user interface, for example a graphical user interface of analysis software.

According to one embodiment, presentation of a data stream (e.g., a stream or set of images, a sequence of pH data, etc.) may be with a bar, for example, a color bar that that may be displayed, for example, on a monitor 18 perhaps through a graphical user interface, or, for example, in real time on an LCD display on a receiver 12 as a data stream is being captured. The presentation may include a varying visual representation of a quantity or a dimension representing, for example, a varying quantity captured in a portion of (e.g., an image frame) an in-vivo data stream. In one example the dimension may be color. The presentation may typically be an abstracted or summarized version of image or other data being presented, for example, streamed on a different portion of the display. The presentation may typically include multiple image items or data items such as bars, stripes, pixels or other components, assembled in a continuing series, such as a bar including multiple strips, each strip corresponding to an image frame. For example, a portion of the presentation may represent a summary of the overall color scheme, brightness, pH level, temperature, pressure, or other quantity on a displayed frame or data item.

Figure 2:
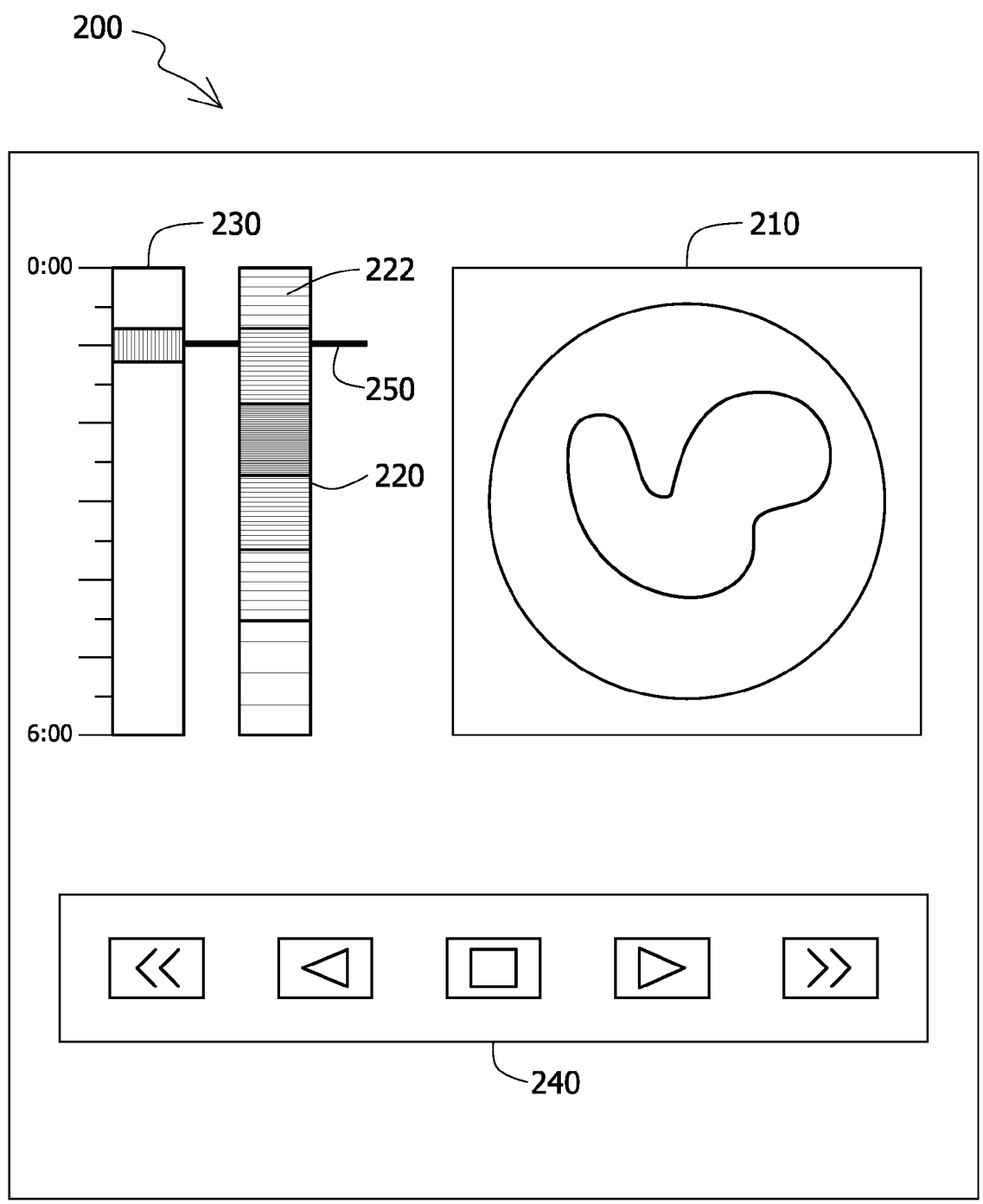
FIG. 2 is a schematic illustration of a display of a color bar together with other data captured in-vivo in accordance with an embodiment of the present invention.

Reference is now made to FIG. 2 showing a display and/or a graphical user interface 200 for displaying data captured in-vivo data. Display 200 may include a summarized graphical presentation 220 of an in-vivo data stream, for example, a color bar. Typically, the graphical presentation 220 may be a fixed presentation displayed alongside a streaming display of a data stream 210, for example, an image stream in accordance with some embodiments of the present invention. In other embodiments of the present invention, graphical presentation 220 may be displayed separately. The graphical presentation 220 may include a series of colors, a series of colored areas, or a series of patterns, image items, images or pixel groups (e.g., a series of stripes 222 or areas of color arranged to form a larger bar or rectangular area), where each, for example, color in the series 222 may be associated with and/or correspond to an element or a group of elements in the original data stream. For example, each colored stripe 222 may correspond to an image or a group of images from a data stream 210. Image units other than stripes (e.g., pixels, blocks, etc.) may be used, and the image units may vary in a dimension other than color (e.g., pattern, size, width, brightness, animation, etc). One image unit (e.g., a stripe 222) may represent one or more units (e.g., image frames) in the original data stream. Typically, the series of, for example, colors in the bar may be arranged in the same sequence or order in which the data stream, for example, the images or groups of images may typically be displayed. In one embodiment of the present invention, pointing at a stripe in a graphical presentation 220 may advance the image stream to the frames corresponding to that stripe.

The color bar may be generated by, for example, assigning a color to each element (e.g., an image frame) or subgroup of elements in the data stream and then processing the series of colors, for example such that it may emphasize variations within the displayed properties. In one embodiment of the invention, it may be processed, for example to emphasize cue points in an accompanying video such that, for example, it may be used as an ancillary tool for indicating points of interest. In one embodiment of the invention, a stream of data 210 may be displayed along side one or more bars and/or graphical presentations (220 and 230) described herein. The data stream 210 may be for example data represented in the graphical presentation 220 (e.g. a captured in-vivo image stream) or other data obtained and/or sampled simultaneously or substantially simultaneously with the data represented in the graphical presentation 220. In one example, a marker or indicator 250 may progress across or along the graphical presentation 220 as the substantially corresponding datum in data stream 210 (e.g., video) may be concurrently displayed to indicate the correspondence between the graphical presentation 220 and the data stream 210. In other embodiments of the invention, the presentation may be of a shape other than a bar, for example a circle, oval, square, etc. According to other embodiments, the presentation may be in the form of an audio tract, graph, and other suitable graphic presentations.

An indicator 250 such as a cursor may advance along the time bar 230 and graphical presentation 220 as the image stream 210 is scrolled on the display 200. In one example, control buttons 240 may be included in the display that may allow the user to, for example, fast-forward, rewind, stop play or reach the beginning or end of, for example, an image stream 210. In other embodiments of the present invention, a user may control the display of a data stream 210, for example, by altering the start position of the streaming display, e.g. skipping to areas of interest, by moving the position of indicator 250, for example with a mouse or other pointing device. In other embodiments of the present invention, a user and/or health professional may insert indications or markers such as thumbnails to mark location along the image stream for easy access to those locations in the future. For example, a health professional may mark these milestones on the graphical presentation 220 (e.g., using a pointing device such as a mouse, a keyboard, etc). Some embodiments described in Published United States patent application US-2002-0171669-A1, entitled "System and method for annotation on a moving image", published on Nov. 21, 2002, assigned to the assignee of the present invention and incorporated by reference herein in its entirety, include methods and devices to mark or annotate portions of an image stream; such methods may be used in conjunction with embodiments of the present invention. Other suitable methods for marking or annotating a stream of data may be used. A user may then "click" on the thumbnails to advance to the site of datum, for example the image frame, of interest or alternatively click on the graphical presentation 220 to advance or retract to the image frame, of interest and then, for example, continue or begin streaming and/or viewing the data stream from that desired point of interest.

Thumbnails or other markers may be defined based on an image of interest from the data stream 210, based on a location identified on the graphical presentation 220 or based on a time recorded on time bar 230. Other suitable methods of defining thumbnails or other markers or notations may be used. For example, a computer algorithm may be used to identify thumbnails that may be of interest to, for example, the health professional. Algorithm based thumbnails may also, for example, be based on an image of interest from the data stream 210, based on a location identified on the graphical presentation 220 or based on a time recorded on time bar 230, or other methods. In other embodiments, the graphical presentation 220 may be in itself a series of color thumbnails, so that a user may point or "click" on colors in the color bar to restart the display of the data stream from a different point in the stream.

Figure 3:
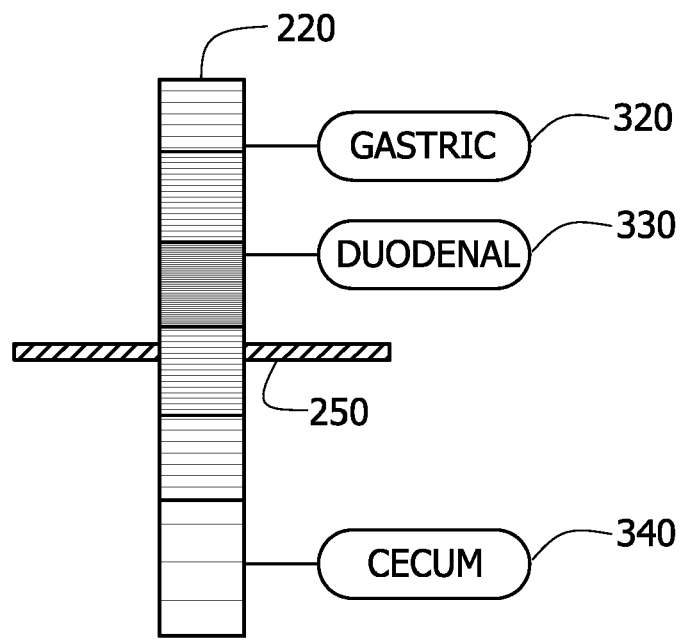
FIG. 3 is a schematic illustration of a color bar with an identified anatomical site in accordance with an embodiment of the current invention.

FIG. 3 is a schematic illustration of a tissue color bar according to an embodiment of the present invention. Tissue graphical presentation 220 may have been obtained through image processing of a stream of images obtained, for example, from an imager 46 imaging the tissue of the GI tract. Other lumens may be sensed, and other modalities (e.g., temperature) may be sensed. The tissue graphical presentation 220 represents, for example, a compressed and perhaps smoothed version of the image stream captured such that the top horizontal strip of color on the bar may represent a first image, a first representative image, or a first group of images captured and the bottom horizontal strip of color may represent the last image, the last representative image, or a final set of images captured; in alternate embodiments only a portion of the image stream and/or other data stream may be represented.

In one embodiment of the present invention, the color scheme of image frames taken of tissue over time may change, for example as an in-vivo imaging device 40 travels along the GI tract. Changes in the color scheme of the images may be used to identify, for example, passage through a specific anatomical site, for example, the duodenal, cecum or other sites, and/or may indicate pathology, for example bleeding or other pathology. When presenting an image stream of a tissue in a summarized, concise color bar, the changes in color streams may be readily identified. For example, passage into the cecum may be identified by a color that may be typical to the large intestine, for example, a color that may indicate content or a color typical of the tissue found in the large intestine. Entrance into the duodenum may be identified by another color that may be typical of the tissue in the small intestine. Other anatomical sites may be identified by observing color and/or changing color streams on a color bar, for example, a tissue color bar. In other embodiments a pathological condition, such as for example, the presence of polyps, bleeding, etc., may be identified by viewing, for example, a tissue graphical presentation 220. A specific area of interest, such as pathology indicated by blood, may be directly identified through the tissue. As such a health professional may first examine the tissue graphical presentation 220 and only afterwards decide what block of images to review. In some embodiments of the present invention, an algorithm may be employed to identify anatomical sites, pathologies, or areas of interest using data from such a color bar and bring them to the attention of a health professional, by for example marking the area of interest along the displayed color bar. A health professional may use the thumbnails or markings along a tissue color bar, for example, markings and/or markings of the first gastric image 320, the first duodenum image 330 and the first cecum image 340 to locate where along the GI tract the data 210 (concurrently being displayed) may be originating from. Knowing the area at which an image was captured may help a health professional decide if an image viewed is representative of a healthy or pathological tissue, and may help a health professional to determine other conditions.

According to some embodiments, different colors or other visual indications, shades, hues, sizes or widths, etc. may be artificially added to a processed data stream, for example, in order to accentuate changes along the data stream. Other processing methods may be used to enhance the information presented to the user. In one embodiment of the invention smoothing may or may not be performed on selected pixels based on decision rules. For example in one embodiment of the invention smoothing may not be performed on dark pixels or on green pixels that may indicate content in the intestines.

Figure 4A:
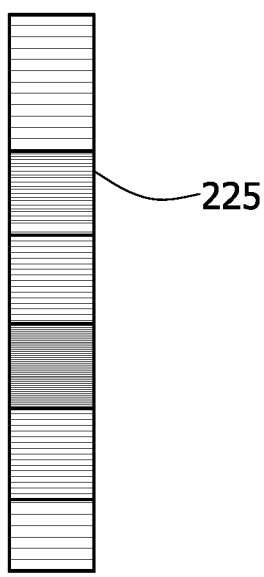
FIGS. 4A and 4B are schematic illustrations of exemplary pH and blood detecting color bars respectively in accordance with embodiments of the present invention.
Figure 4B:
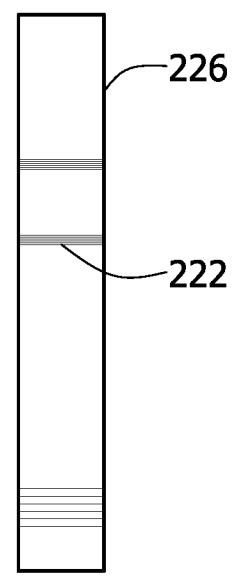

Reference is now made to FIGS. 4A and 4B showing an example, of graphical presentations in the form of a bar other than tissue color bars. For example, FIG. 4A shows a schematic example of a pH color bar 225 that may map out pH measurements obtained, for example over time or alternatively along a path of a body lumen. Other measurements may be used, for example, temperature, blood sensor, and pressure measurements may be used. Data obtained from an in-vivo pH sensor may be displayed with color, brightness, and/or patterns to map out the pH over time and/or over a path, for example a GI tract where different colors may represent, for example, different pH levels. In other examples, different colors may represent different levels of changes in pH levels. Other suitable presentations may be displayed. Changes in pH along a path may be due to pathology, entrance into or out of anatomical locations, etc. Observed changes in pH over time may, for example, classify physiological occurrences over time, for example a healing process, progression of a medical condition, etc. FIG. 4B is a schematic illustration of blood detecting color bar 226. In one example, color stripes 222 along the bar may indicate a site where blood may have been detected.

In one embodiment of the present invention, color bar 226 may give indication of the presence of blood over a period of time. International application published as WO 02/26103 entitled "An immobilizable in vivo sensing device" assigned to the assignee of the present invention which is incorporated by reference herein in its entirety includes, inter alia, descriptions of embodiments of devices, such as capsules, that may be anchored at post-surgical sites. Embodiments described in International application WO 02/26103 may be used in conjunction with the system and methods described herein to capture and transmit data for an in-vivo site over time. A presentation of the captured data, for example a color bar may give indication of any changes occurring over time from a current static situation or may show an overview of how a tissue healed or changed over time without having to review the entire stream image by image.

Figure 5:
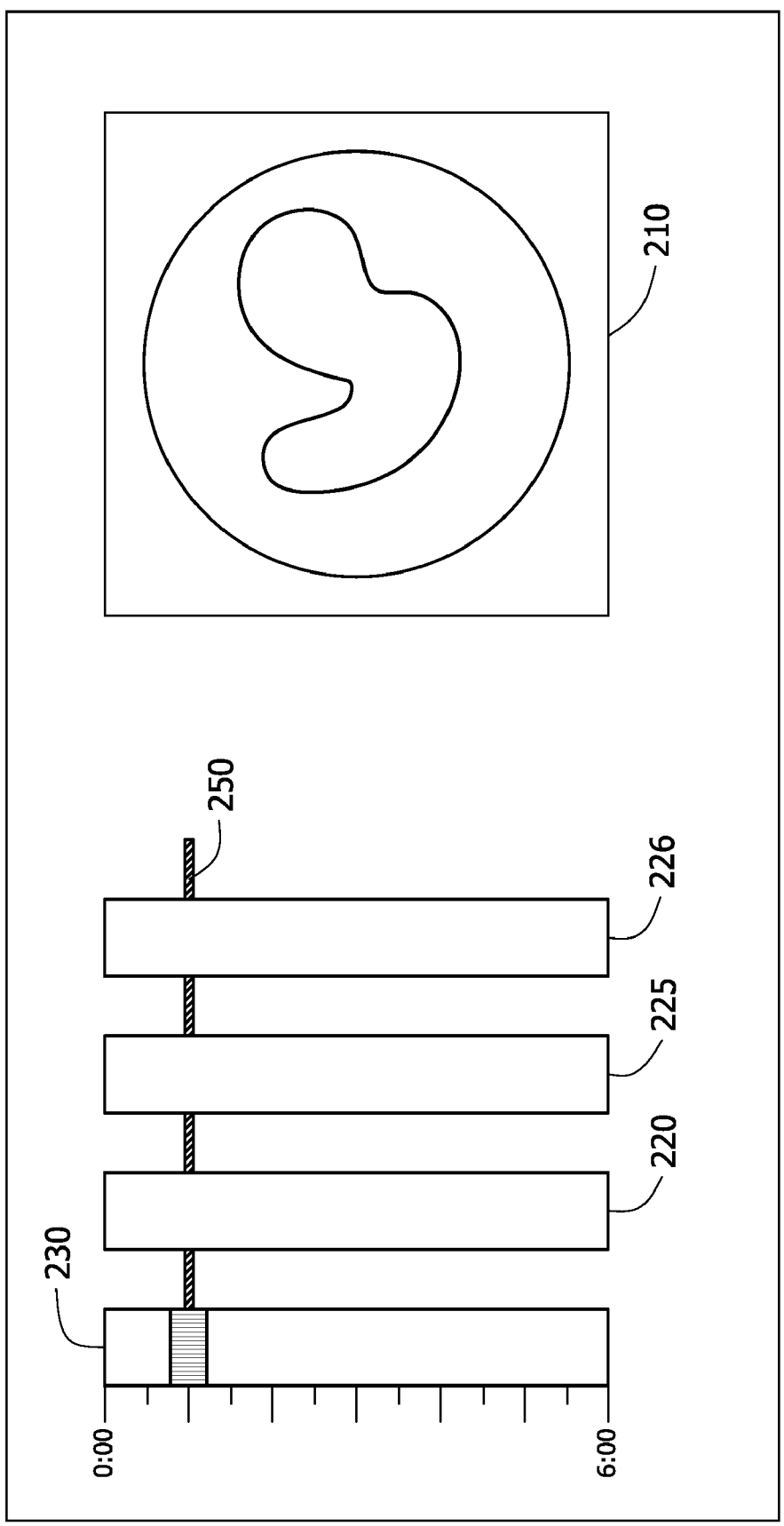
FIG. 5 is a display with more than one color bar that may be viewed substantially simultaneously according to an embodiment of the present invention.

Reference is now made to FIG. 5 showing schematically a graphical user interface for viewing a streaming display of in-vivo data 210 along with multiple fixed summarized graphical presentations 220, 225, and 226 of a data stream. A single scrolling indicator 250 may be used along with a time bar 230 to point to a position along the fixed presentation of the data streams (220, 225, and 226) so as to indicate where along the bars the data 210 presently being displayed originated. The individual color bars may include for example, a tissue graphical presentation 220, a pH color bar 225, and a blood detector color bar 226. Other number of graphical presentations, other suitable types of bars summarizing other data, and other suitable types of presentations may be used. Multiple graphical presentations may be helpful in diagnosis of medical conditions as well as locating within a stream of data, sites of interest. Multiple graphical presentation may increase the parameters that are available to a health professional when reviewing, for example, an image stream and may give a better indication of the environmental condition that may exist at a point of observation. For example, in one embodiment, pH, temperature and tissue graphical presentations or other presentation may be displayed, possibly, side by side. In an alternate embodiment, two or more streams of information may be displayed simultaneously and combined into a single graphical presentation using for example a unifying algorithm. For example, pH and temperature can be combined into a single color bar where, for example, red holds the temperature values and blue holds the pH values (other suitable colors may be used). A physician may choose which parameters he/she is interested in viewing as a map or summary. Having more than one set of parameter available at one time may make it easier to find more anatomical sites and to identify areas that may, for example, contain pathologies. Numerous algorithms based on case studies or other suitable data may be applied to suggest to the physician alert sites or other information obtained from one or more color bars or from the combination of one or more color bars. Other suitable indicating maps, information summaries, or color bars may be used.

Non-limiting examples of different types of graphical presentations (e.g., color bars, series of brightness levels, etc.) may include:

Tissue graphical presentation: brightness, pattern, or other visual representation of a tissue image stream;

Temperature graphical presentation: color, brightness, pattern, or other visual representation of sensed in-vivo temperature data over time and/or along a body lumen;

PH graphical presentation: color brightness, pattern, or other visual representation of sensed in-vivo temperature data over time and/or along a body lumen;

Oxygen saturation graphical presentation: color, brightness, pattern, or other visual representation of sensed oxygen saturation over time and/or along a body lumen;

Pressure graphical presentation: color, brightness, pattern, or other visual representation of sensed in-vivo pressure over time and/or along a body lumen;

Blood detection graphical presentation: color, brightness, pattern, or other visual representation of sensed presence of bleeding over time and/or along a body lumen;

Biosensor graphical presentation: color, brightness, pattern, or other visual representation of results obtained from one or more in-vivo biosensors;

Speed graphical presentation: color, brightness, pattern, or other visual representation of the speed of a moving in-vivo device;

Spatial position graphical presentation: color, brightness, pattern, or other visual representation of the spatial position and/or orientation of an in-vivo device over time;

Ultrasound graphical presentation: color, brightness, pattern, or other visual representation of data sensed from an in-vivo ultrasound probe; and Motility graphical presentation: color, brightness, pattern, or other visual representation of the sensed motility of a traveling in-vivo device.

International application published as WO02102223, entitled "MOTILITY ANALYSIS WITHIN A GASTROINTESTINAL TRACT" assigned to the assignee of the present invention and incorporated by reference herein in its entirety includes, inter alia, a device, system, and methods for determining in-vivo motility that may be used in conjunction with the device, system, and method described herein. Other suitable representations other than bars and other suitable types of data may be implemented using the device, system, and method described herein.

Figure 6:
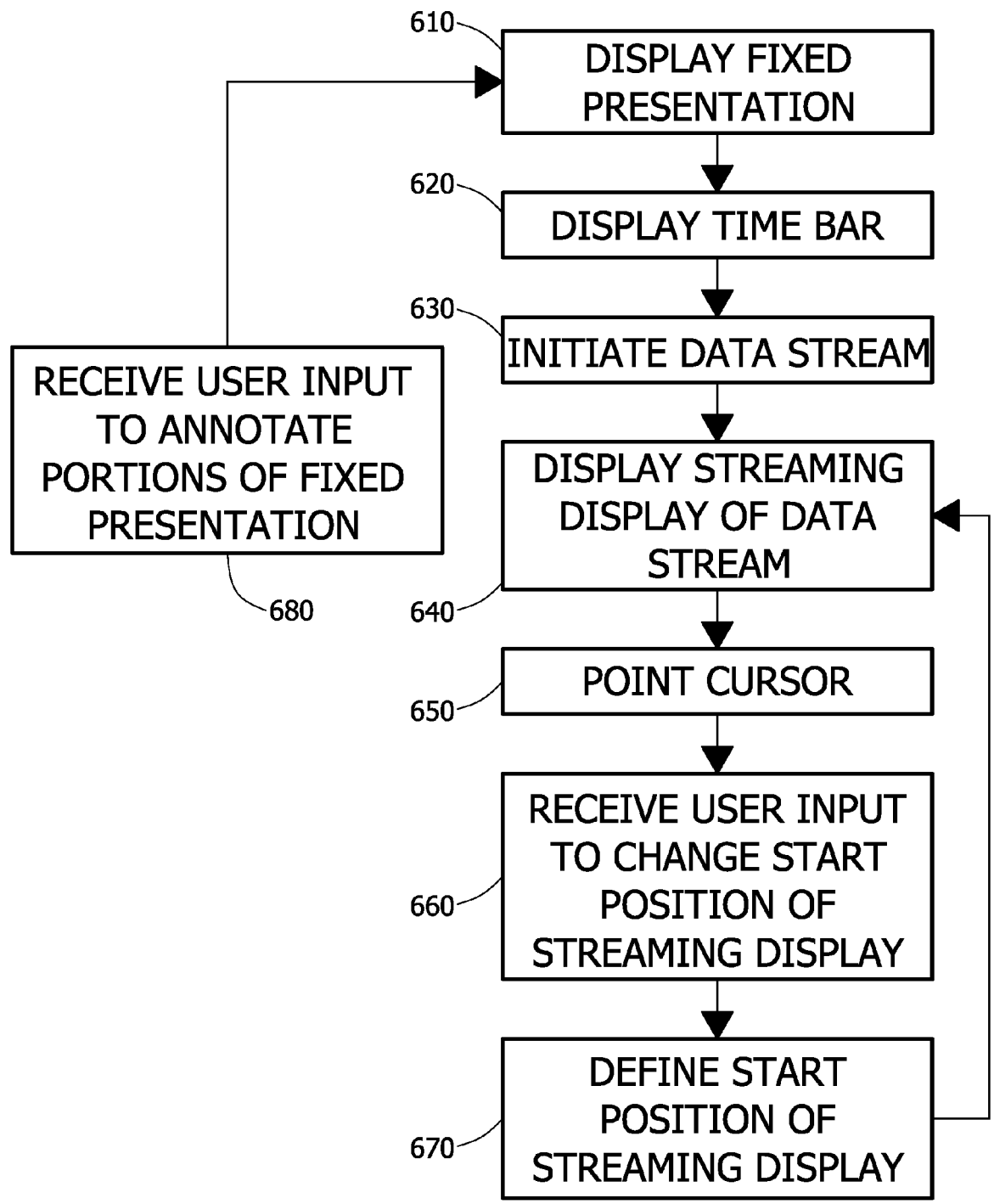
FIG. 6 is a flow chart describing a method for presentation of in-vivo data according to an embodiment of the present invention.

Reference is now made to FIG. 6 showing a flow chart of a method for presentation of an in-vivo data stream according to an embodiment of the present invention. In block 610 a fixed presentation of a data stream may be displayed, e.g. a color bar, a series of strips of varying width or brightness, etc., summarizing, for example, an image stream, a pH data stream, temperature data stream etc. A user may annotate portions of the fixed presentation (block 680) for example identified anatomical sites and/or physiological events. More than one fixed presentation may be displayed. In block 620 a time bar indicating the time that data from a displayed data stream may have been sampled and/or captured may be displayed. A time bar need not be used. The data stream to be displayed may be initiated (block 630) so as, for example, to begin the streaming display. In block 640, streaming of the data stream may begin. The displayed data stream may be other than the data stream represented in the fixed presentation. For example, an in-vivo device may capture images as well as sample, for example, temperature values, as it progresses through the body lumen. In one example, a fixed presentation of temperature values may be displayed along side a streaming display of image frames captured substantially simultaneously. In other examples, the fixed presentation as well as the streaming display may be of the captured image frame. In block 650 as the data stream progress, a cursor or other indicator may point to a position on the fixed presentation (as well as the time bar) that may correspond to the data (e.g., an image frame, a pH value) displayed in the displayed data stream. In block 660, a command may be received to stream the display from a different point in the data stream. In one example, the user may drag the cursor along the fixed presentation to indicate the point at which the streaming should begin. In other examples, the user may annotate portions in the fixed presentation (block 680) and at some point click on the annotations to begin streaming the data stream at the corresponding point in the displayed streamed data stream. Other suitable methods of receiving user inputs may be implemented and other suitable methods of annotations other than user input annotations may be implemented, for example as may have been described herein. In block 670 the start position of the streaming display may be defined by a user input and with that information a command to begin streaming from the defined point may be implemented. Other operations or series of operations may be used.

Figure 7:
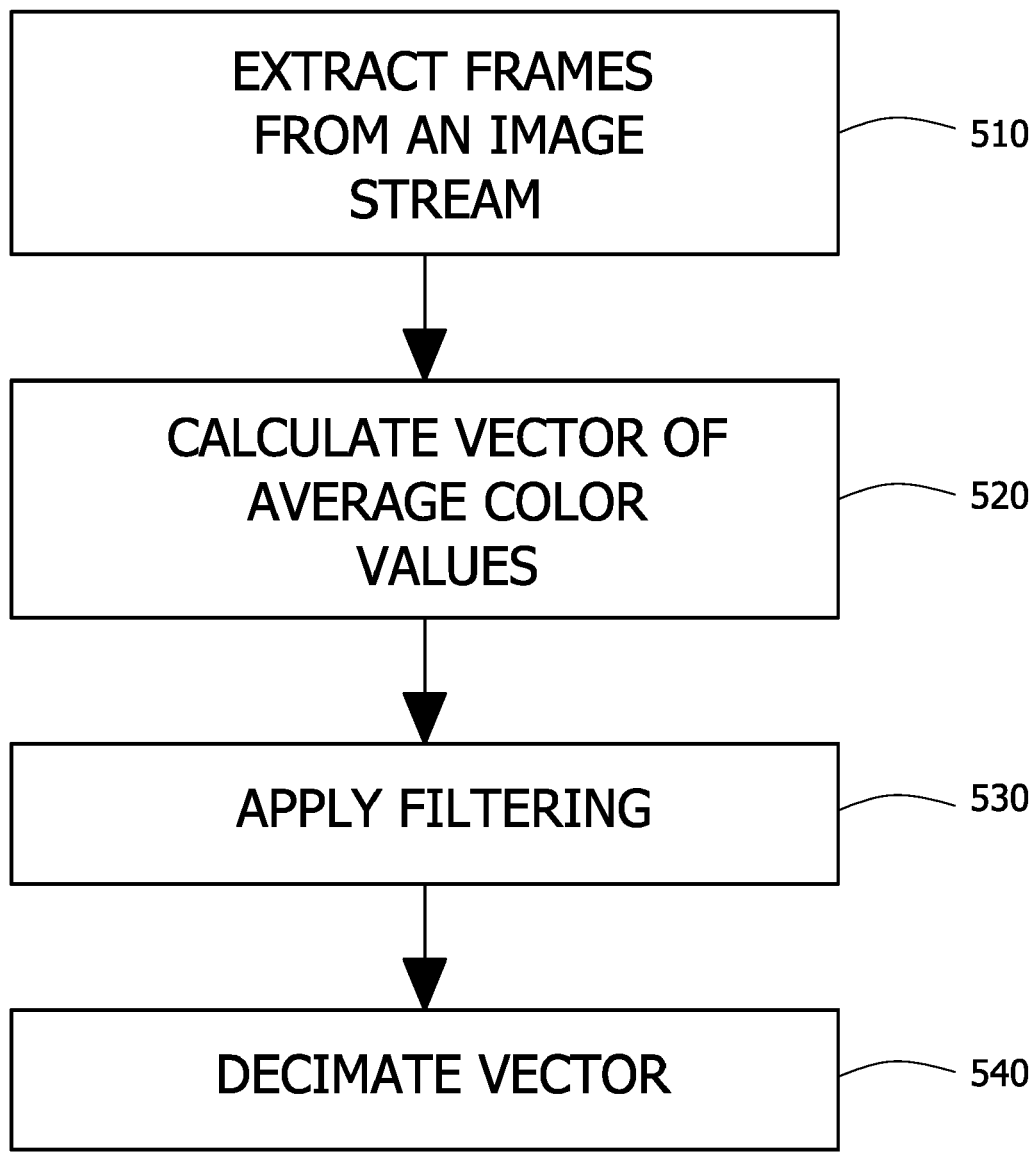
FIG. 7 is a flow chart describing a method for constructing a color bar from a stream of images in accordance with an embodiment of the present invention.

Various suitable methods may be use to abstract data from the source data stream (e.g. an image stream, a series of temperature data) to the fixed representation. Reference is now made to FIG. 7 describing a method of generating a fixed summary of a data representation, for example a tissue color bar, according to an embodiment of the present invention. In an exemplary embodiment, in block 510 a set (wherein set may include one item) or series of data items, for example frames from an image stream may be extracted. For example every $10^{th}$ frame from the image stream may be extracted and/or chosen to represent the image stream in a fixed presentation. In other embodiments, all the data items or frames may be included, or every $5^{th}$, $20^{th}$, or any other suitable number of frames may be used. In yet other embodiment of the present invention, an image representing an average of every two or more frames may be used. In one example, a criterion may be defined by which to define one frame out of a block of frames (e.g. two or more frames) to be representative of that block. In block 520 a vector of average color or other values (e.g., brightness values) may be calculated. In one embodiment of the present invention, the average color is calculated in a defined area in each frame, for example, a defined area that is smaller than the area of the image frame. For example, an average red, blue, and green value in a defined area of each frame in the series of frames chosen may be calculated to form 3 color vectors. In one example, the defined area may be a centered circle, for example with a radius of 102 pixels taken from an image frame containing, for example 256×256 pixels. In other examples, only one or two colors may be used to generate a color bar. In block 530 a filter may be applied, for example a median filter, on the vector of average color values, for example, the three color vectors: red, green, and blue. An exemplary filter may for example have a length defined by the following equation:

$$1+2(\text{alpha} *N/Np); \text{alpha} =2.2;$$

where N is the original pixel size and Np is the desired pixel size of the resultant tissue color bar presentation. Other equations or formulae may be used.

In block 540 the pixel size of the resultant tissue color bar presentation may be set by decimating the vector of colors to a desired size, for example, decimating each color vector to the desired size by interpolation.

Other methods of generating a tissue color bar or other data summary may be implemented. In one embodiment, a series of data items, such as for example one or more individual images, may be converted to a data point, such as a color area or a color strip within a larger display area, such as a color bar. An average brightness value for each image or set of images may be found, and a bar or assemblage of strips of widths, patterns, colors or brightnesses corresponding to the averaged values may be generated. The values such as pH, pressure or temperature corresponding to each of an image or set of images (e.g., in a device collecting both image and other data) may be found, and a bar or assemblage of strips or other image units of widths, colors or brightnesses corresponding to the averaged values may be generated. One or more images may be converted or processed to a corresponding stripe of color.

Various data items may be combined together to individual data points using, for example, averaging, smoothing, etc. In one embodiment the luminance of the images can be normalized and only normalized chromatic information of the data for example the tissue's color, can be shown, eliminating, for example, the contribution of the light source. Other color bars or other presentations of data obtained in-vivo other than imaged data may be generated.

Color bars and other representations of data may aid in reducing the viewing time necessary to review an image stream. A health professional may, in one embodiment of the present invention, use a pointer, for example, a mouse to point at an area along the color bar that may be of interest. The graphical user interface may in turn skip to the corresponding location on the data stream, so that a health professional may focus into the area of interest without having to review an entire image stream. A health professional may for example, change the rate at which to view different portions defined by a tissue color bar. A specific area of interest, such as pathology indicated by blood, may be directly identified through the tissue. As such a health professional may first examine the tissue color bar and only afterwards decide what block of images is the interested in reviewing. When screening patients it may be possible only to review one or more data presentations, such as a tissue color bar. In other examples, a summarized graphical presentation of a data stream may be generated in real time in for example a recorder 12, and displayed in real time on a display included in recorder 12.

In other embodiments of the present invention, a graphical presentation, for example, color bar may be used for other purposes besides presentation of in-vivo data. For example, a color bar may be used as a summarizing presentation of any stream of frames, for example a video. A summarized graphical presentation, for example a color bar as described herein, of a video may help a viewer to locate different scenes in a video and possibly fast forward, rewind or skip to that scene. For example, a scene in a movie that might have been filmed outdoors may for example have a different color scheme than a later or earlier scene that may have been filmed indoors. The color bar may be analogous to a color table of contents.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for generation of a color summary of a stream of color frames captured by an ingestible imaging capsule, the method comprising:
using a computing device:
   extracting frames from a stream of image frames captured by an ingestible imaging capsule;
   calculating a vector of average color values of the extracted frames;
   applying a filter on the vector of average color values;
   generating a color bar using the filtered vector; and
   displaying the color bar.

2. The method according to claim 1 wherein extracting frames from said stream comprises selecting every $n^{th}$ frame from the stream.

3. The method according to claim 1 wherein extracting frames from said stream comprises selecting a frame representing a block of frames.

4. The method according to claim 1 wherein extracting frames comprises extracting all the frames from the image stream.

5. The method according to claim 1 wherein calculating the vector of average color values of the extracted frames comprises calculating an average color of a defined area of each frame.

6. The method according to claim 1 wherein the filter is a median filter.

7. The method according to claim 1 comprising decimating the filtered vector of average color values to a desired size.

8. A system for generation of a color summary of a stream of color frames captured by an ingestible imaging capsule, the system comprising:
a computing device to:
   extract frames from a stream of image frames captured by an ingestible imaging capsule;
   calculate a vector of average color values of the extracted frames;
   apply a filter on the vector of average color values; and
   generate a color bar using the filtered vector of average color values; and
a display to display the color bar.

9. The system according to claim 8 wherein extracting frames from said stream comprises selecting every $n^{th}$ frame from the stream.

10. The system according to claim 8 wherein extracting frames from said stream comprises selecting a frame representing a block of frames.

11. The system according to claim 8 wherein extracting frames comprises extracting all the frames from the image stream.

12. The system according to claim 8 wherein calculating the vector of average color values of the extracted frames comprises calculating an average color of a defined area of each frame.

13. The system according to claim 8 wherein the filter is a median filter.

14. The system according to claim 8 comprising decimating the filtered vector of average color values to a desired size.

* * * * *